United States Patent [19]
Said et al.

[11] Patent Number: 5,688,291
[45] Date of Patent: Nov. 18, 1997

[54] COMPOSITION FOR SIMULTANEOUSLY LIGHTENING AND COLORING HAIR

[75] Inventors: Hayel Said; Hian Said, both of Simi Valley, Calif.

[73] Assignee: L'Avante Garde, Inc., Simi Valley, Calif.

[21] Appl. No.: 671,213

[22] Filed: Jun. 27, 1996

[51] Int. Cl.$^6$ .................................................. A61K 7/13
[52] U.S. Cl. .................. 8/431; 8/405; 8/662; 8/675; 8/107; 8/110; 8/931
[58] Field of Search ........................ 8/405, 431, 675, 8/107, 662, 110, 931

[56] References Cited

U.S. PATENT DOCUMENTS

| | | | |
|---|---|---|---|
| 2,991,228 | 7/1961 | Lustig | 424/62 |
| 3,193,464 | 7/1965 | Edman et al. | 424/62 |
| 3,578,387 | 5/1971 | Zviak | 8/407 |
| 3,679,347 | 7/1972 | Brown | 8/431 |
| 3,912,446 | 10/1975 | Zviak | 8/425 |
| 4,185,958 | 1/1980 | Baugaut et al. | 8/431 |
| 4,425,132 | 1/1984 | Grollier et al. | 8/405 |
| 4,781,724 | 11/1988 | Wajaroff et al. | 8/426 |
| 4,801,303 | 1/1989 | Carlough et al. | 8/532 |
| 5,224,964 | 7/1993 | Shami | 8/405 |
| 5,226,924 | 7/1993 | Junino et al. | 8/405 |
| 5,340,367 | 8/1994 | Schultz et al. | 8/405 |
| 5,374,288 | 12/1994 | Prota et al. | 8/406 |

FOREIGN PATENT DOCUMENTS

| | | |
|---|---|---|
| 1137355 | 12/1968 | United Kingdom . |
| 1554331 | 10/1979 | United Kingdom . |
| 2217735 | 11/1989 | United Kingdom . |

OTHER PUBLICATIONS

Derwent Abstract of SU 492,283, Ukrbytkhim, Dec. 1975.

Colour Index Third Edition, vol. 4; pp. 4018, 4537 and 4557; CI Nos. 11210, 64500, 61105 and 61110, 1971 (no month available).

*Primary Examiner*—Ardith Hertzog
*Assistant Examiner*—Caroline L. Dusheck
*Attorney, Agent, or Firm*—Oldham & Oldham Co., L.P.A.

[57] ABSTRACT

In accordance with the present invention, there is provided a single-step process and composition of a category-2 hair bleach which can simultaneously lighten the hair up to seven levels, and effectively neutralize any undesirable warmth that accompanies the lightening process. This is achieved by including in the bleach composition disperse dye molecules which the present invention has found to be both, stable in the bleach, and capable of depositing the desired amount of various permanent tones on the hair. These disperse dyes do not stain the scalp of the client or the hands of the hairdresser, but are substantive only to the hair fibers. The dyes fall into the classes of anthraquinones and azo compounds.

12 Claims, 2 Drawing Sheets

COMPOSITION FOR SIMULTANEOUSLY LIGHTENING AND COLORING HAIR

TECHNICAL FIELD

The invention described herein pertains generally to hair bleach compositions capable, in a single step, of lightening hair color by as much as seven levels while simultaneously depositing permanent tones that may, either neutralize the warmth generated by the bleaching treatment, or add other desirable colors to the lightened hair.

BACKGROUND OF THE INVENTION

Natural hair color is derived from melanin granules embedded throughout the cortex of hair fibers. Two general classes of such pigments have been identified: eumelanins (brownish black) and pheomelanins (reddish orange). The combination ratio and concentration of these two types of pigments impart to the hair its characteristic natural gradations of color. Dark hair has a higher concentration of the eumelanins, while red hair has a predominance of the pheomelanins. Light blond hair has reduced amounts of both.

Human hair is arbitrarily assigned a scale often levels to describe its darkness (or lightness). Black hair is designated as level one, medium brown hair as level five, and pale light blond as level ten, with several nuances in-between.

Hair bleaching is a chemical process by which the melanin pigment granules are gradually destroyed by the bleaching agent, resulting in lighter hair color. The melanin pigments are not all lightened at the same rate. The eumelanins are easier to break down than the pheomelanins. Because of this property, dark hair, when bleached, experiences preferential destruction of the melanin pigments, which leads to the visual enhancement of the red pigments, and the casting of an undesirable warm reddish orange or "brassy" tone to the bleached hair. In order to neutralize this warmth, hair colorants of a drabbing nature are almost always applied during or after a bleaching treatment.

Based on their chemical composition and their strength, hair bleaches may be classified into two categories:

1. Category-1 Bleaches: These, generally, are mild liquid- or creme-based compositions utilizing alkaline hydrogen peroxide solutions as the main oxygen-generating agent to oxidize and bleach the melanin, usually in conjunction with a hair coloring process. Just before use, the peroxide is mixed with an alkalizing agent such as ammonia, and the resulting liquid or creme is applied to hair for 30 to 60 minutes. Such compositions may lighten the hair by as much as 4 levels at the most, depending on the concentration of hydrogen peroxide used. For example, a level-6 hair may be lightened, under favorable conditions, to a level 10.

2. Category-2 Bleaches: These are mostly powder compositions based on persulfate salts (ammonium, potassium, sodium) as auxiliary or booster supplies of active oxygen, and silicate and/or carbonate salts as sources of alkalinity. Again, just before use, they are mixed with hydrogen peroxide solutions to form a workable creme that can be applied to the hair. Some powder bleaches even have the hydrogen peroxide itself incorporated in a solid form such as urea peroxide. Quite often, a third separately-packaged component, referred to as a bleach oil which may contain humectants and other conditioning agents, is added to the bleach powder and peroxide at time of use.

Category-2 bleaches can deliver over seven levels of lift, something which cannot be attained with category-1 bleaches. They are usually utilized whenever more than four levels of lift are desired, such as when lifting a level-5 hair, or darker, to a pale blond.

Because of the underlying warm tones that are exposed at various levels of bleaching, hair lightening, as mentioned above, is generally accompanied by a toning process to neutralize the warmth and give the hair a pleasant natural look. The toning process itself is a rather delicate one. Toners fall into three hues: blue, green and violet, generally known as drabbing or ashing hues. These hues, or combinations of, are required to neutralize the spectrum of undertones that are exposed during the lightening process. Dark blond hair, for example, would expose yellow undertones upon bleaching. Therefore, according to the law of color, a violet-based toner would neutralize the yellowish tone to result in a platinum or silver blond shade. The concentration of the toner should be adjusted so that the lift is not masked by the deposition of color. Similarly, medium brown hair would reveal a significant amount of orange undertones, requiring a significant amount of a blue-based toner. Dark hair, when bleached, exhibits reddish-orange undertones requiring a bluish-green toner.

Category-1 bleaches constitute most of what is known as the high-lifting shades of commercial permanent hair colorants. They have inherent toners mostly in the form of oxidative dyes. Some may contain Direct, Disperse, Acid, or Basic dyes, or combinations thereof. The prevailing alkaline peroxide environment of this category of bleaches is mild enough to allow for the survival of several types of dyes. Therefore, the limited lightening of hair pigments and the deposition of neutralizing toners is a simultaneous process which is completed in about one hour.

In category-2 bleaches, the medium is quite intolerant to most dyes. The combination of higher alkalinity and stronger oxidizing conditions act synergistically to destroy these dyes within a short period of time. Unlike the abundance of colorants surviving category-1 bleaches, no useful dyes have been identified to date which are both, stable in powder bleaches, and capable at the same time of dyeing hair efficiently.

There is an abundance of patents issued in the area of regular oxidative hair coloring compositions. Most of these patents pertain to the synthesis of new dyes, as well as to development of new ingredients which improve on color deposition and longevity. For example, U.S. Pat. No. 3,578,387 disclosed the use of water-soluble Direct dyes in conjunction with Disperse dyes in a category-1 bleaching medium consisting of hydrogen peroxide and ammonia. Similarly, U.S. Pat. No. 3,912,446 disclosed the use of Acid dyes in a similar bleaching composition.

The patent literature includes only a few references in relation to compositions that simultaneously lighten the hair by more than four levels and deposit drabbing hues at the same time. The few patents that have been issued relate to bleaching compositions that utilize various types of pigments which, although stable in a category-2 bleaching medium, are unable to deposit significant drabbing hues useful in neutralizing the warm undertones of the hair. Pigments in general, as defined by the Color Index (volume 3, 1971, page 3267), are insoluble colorants. They are usually high molecular-weight and bulky molecules which cannot penetrate the hair fiber very easily and are unable to color the hair. U.S. Pat. No. 2,991,228 disclosed the use of a blue pigment of the metal phthalocyanine family in a bleach powder, which imparted a blue color to the bleach mixture in the bowl. The pigment, while imparting a stable blue color to the bleach mixture, does not deliver significant tonal benefit to the hair (See FIG. 5 below). Similarly, U.S. Pat. No. 3,193,464 disclosed the use of metal-complex azo dyes of 2:1 ratio (two dye molecules complexed with one metal atom). These metal complexes provide only weak temporary tints which wash off the hair after only a few shampoos.

Recently, U.S. Pat. No. 5,224,964, disclosed a powder bleach composition containing pigment-type colorants such as those used in "finger paint" and silk screening. As mentioned above, the tonal effect of these pigments is very poor. This fact, which is demonstrated in FIG. 5 below, is also confirmed in the patent itself (Example 4, column 5) where these pigments fail to color unbleached hair. Example 7, column 6, of the same patent, also indicates that the use of these colorants in conjunction with the bleach did not eliminate the reddish and gold undertones, but resulted in "less red" and "less gold" on medium brown hair.

Because of the lack of an effective category-2 toning bleach on the market, salons still resort to a two-step process whereby they pre-lighten the client's hair with a powder bleach (category-2) and then follow, in an independent treatment, with a toner in the form of oxidative hair color (category-1) to impart to the hair a cool natural look.

The advantages of a category-2 bleach with a built-in effective toner are significant. First, a single-step product will significantly reduce the time of the hair lightening process, a feature which appeals to both, the client and the salon operator. Second, It reduces the chances of scalp irritation due to prolonged contact of the skin with alkalinity, peroxide and oxidation dyes. And third, the single-step application significantly reduces the damage to the hair because it eliminates the need for additional alkaline peroxide treatments.

SUMMARY OF THE INVENTION

In accordance with the present invention, there is provided a single-step process and composition of a category-2 hair bleach which can simultaneously lighten the hair up to seven levels, and effectively neutralize any undesirable warmth that accompanies the lightening process. This is achieved by including in the bleach composition disperse dye molecules which the present invention has found to be both, stable in the bleach, and capable of depositing the desired amount of permanent ashing tones on the hair in proportion to the degree of warmth. Another added advantage of this invention, is that these disperse dyes do not stain the scalp of the client or the hands of the hairdresser, but are substantive only to the hair fibers.

These and other objects of this invention will be evident when viewed in light of the drawings, detailed description, and appended claims.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION OF THE INVENTION

Figure 3:
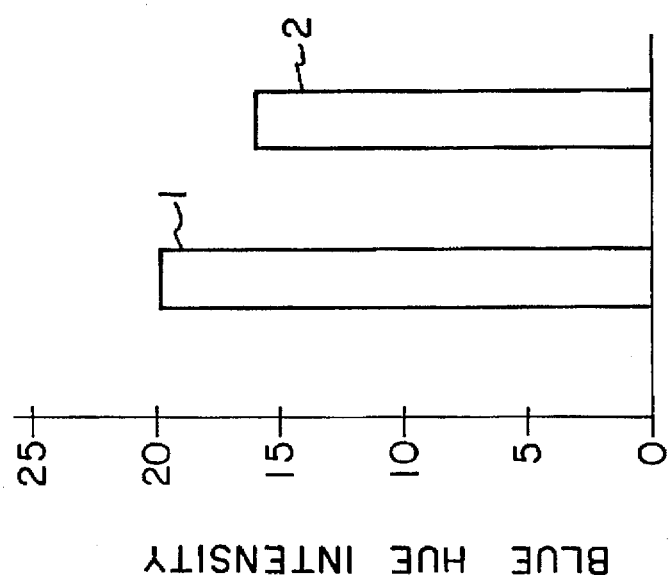
FIG. 3 is a plot of the stability of Disperse Blue 148 in the two bleach mediums of FIG. 1.

The best mode for carrying out the invention will now be described for the purposes of illustrating the best mode known to the applicant at the time. The examples are illustrative only and not meant to limit the invention, as measured by the scope and spirit of the claims.

To achieve the object of the present invention, namely creating a single-step bleach which lightens the hair by more than four levels, and at the same time, neutralizes its undertones, hundreds of colorants belonging to the classes of Direct, Disperse, Basic, or Acid dyes have been tested for three properties: 1). Stability in a category-2 bleach medium. 2). Ability to color the hair. 3). Permanency of the deposited color.

The testing procedure which was employed to screen these dyes consisted of two steps: First, the dye to be tested was incorporated into a commercial bleach powder (Basic White 2) and used in combination with a 6% hydrogen peroxide solution (Clairoxide, 20 volume. Both, Basic White 2 and Clairoxide, are Trade Marks of Clairol, Inc. of Stamford, Conn.). Any other commercial bleach powder and peroxide solution could have served the purpose. The concentration of the dye in the bleach powder was 1% by weight. Twenty grams of this dye-bleach powder blend were added to 40 grams of the peroxide solution and mixed in a plastic bowl. The mixture took on the color of the dye used. Using a brush, the bleach mixture was applied to natural white and medium brown hair swatches, wrapped in aluminum foil, and incubated in an oven at 55° C. (simulating the action of a hair dryer) for 10 minutes. The remaining mixture in the bowl was monitored for any change in color associated with instability. If the oven-treated hair swatches revealed significant color deposit on natural white hair, and if there was no appreciable color break-down in both the foil and the bowl, then another set of swatches would be treated with the same bowl mixture which is left to age for at least 30 minutes on the bench. This is intended to simulate the time required to complete a normal bleach application in the salon. The second set thus obtained, should achieve the same level of color deposit as did the first in order for the dye to be deemed acceptable.

Second, once a dye has been judged to be acceptable in terms of color deposit and stability in bleach, it would be assessed for durability of color under repeated washing. This was achieved by subjecting the treated swatches to twenty cycles of shampooing with a mild shampoo and drying. A color is considered to be permanent if after 20 cycles of washing, 80% or more of the original color intensity is visually retained in the hair.

The greatest majority of the dyes tested, not surprisingly, failed at least one of the three criteria listed above. Efforts to create a single-step full action bleach and toner, have been going on for decades with no success. The end result invariably was the same: Dyes that performed well in a category-1 bleach medium, failed in a category-2 bleach medium.

The present invention has identified a small number of colorants, used heavily in the textile industry, and belonging to the Disperse Class of dyes which performed quite well in the category-2 bleach system. Many of these disperse dyes are relatively new and their chemical structures are trade secrets, and many of their properties constitute proprietary information. Each of these dyes may be distributed under several trade names.

Disperse dyes are only slightly soluble in water. They all are void of sulfonic groups. Yet, this slight solubility is important because it is believed that the uptake of dye molecules by fibers takes place from this aqueous phase (Color Index, Volume 3, 1971, page 2479). Solubility can be modified by the dispersing agents which can deliver very fine dispersions.

The ashing blue Disperse dyes that the present invention found to be of value to the object at hand, are listed in Table 1 below. Each dye is listed under its generic Color Index (CI) name. Some CI numbers are not available because of proprietary information restrictions, but where available, CI numbers are listed as well.

Since green Disperse dyes are very scarce, some Disperse yellow and orange dyes were discovered which delivered good greens in combination with the blues. Similarly, because no strong violets were found, some red Disperse dyes were discovered which yielded intense violets in combination with the blue dyes. Table 1 lists also some of the red, orange and yellow Disperse dyes that were used to create violet and green ashing shades in combination with the blue dyes. When more than one dye was needed to create a certain shade, it was of great importance to identify those dyes with identical diffusion rates and substantivity to the hair. The dyes have been assigned arbitrary units on a scale of 0 to 5 to indicate their bleach performance (i.e. tinctorial ability and stability in category-2 bleach media). A dye with a rating of (5) means outstanding toning features and stability, while a rating of (0) indicates both, lack of toning ability and instability in the bleach medium. Blue and violet dyes with (0) rating are not listed.

This rating system does not reflect in any way the true tinctorial values that these dyes may possess under normal tinting conditions, or when different substrates, such as textiles, are used.

TABLE I

| Dye | Formula/Chemical Class | C.I. # | Toning Ability |
|---|---|---|---|
| Disperse Blue 102 | Azo | | 4 |
| Disperse Blue 106 | Azo | | 4 |
| Disperse Blue 148 | Azo | | 4 |
| Resolin Blue K-FBL | Azo | | 3 |
| Resolin Blue K-2GLS | Azo | | 3 |
| Disperse Blue 154 | Azo | | 2 |
| Disperse Blue 281 | Azo | | 2 |
| Disperse Blue 291 | Azo | | 2 |
| Disperse Blue 321 | | | 2 |
| Disperse Blue 347 | | | 2 |
| Disperse Red 118 | Azo | | 3 |
| Disperse Red 167:1 | Azo | | 3 |
| Disperse Red 179 | Azo | | 3 |
| Disperse Red 338 | Azo | | 3 |
| Disperse Red 54 | Azo | | 2 |
| Disperse Red 258 | Azo | | 2 |
| Disperse Orange 3 | 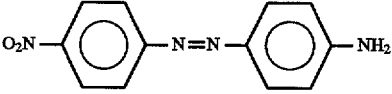 $O_2N-\langle\bigcirc\rangle-N=N-\langle\bigcirc\rangle-NH_2$ | 11005 | 3 |
| Disperse Orange 66 | Azo | | 3 |
| Disperse Yellow 241 | Azo | | 2 |

Table 2 lists those blue and violet Disperse dyes that were stable in the bleach but had weak toning power which was adequate for toning hair types that require only minimal color deposition, such as light brown or dark blond hair. The toning power of these dyes could be slightly enhanced by using larger dye loads, or by adding a third component to the bleach system in the form of a bleach oil containing some dye carriers, surfactants organic solvents such as benzyl alcohol, amyl alcohol, cyclohexanol or any of several solvents that exhibit low water solubility.

TABLE II

| Dye | Formula/Chemical Class | C.I. # | Toning Ability |
|---|---|---|---|
| Disperse Blue 3 | 1-NHCH₃, 4-NHCH₂CH₂OH anthraquinone | 61505 | 1 |
| Disperse Blue 7 | 1,4-bis(CH₂CH₂OH) anthraquinone | 62500 | 1 |
| Disperse Blue 14 | 1,4-bis(NHCH₃) anthraquinone | 61500 | 1 |
| Disperse Blue 26 | 1,5-bis(NHCH₃)-4,8-bis(OH) anthraquinone | 63305 | 1 |
| Disperse Blue 35 | Anthraquinone | | 1 |
| Disperse Blue 55 | Anthraquinone | | 1 |
| Disperse Blue 56 | 1,5-bis(NH₂)-4,8-bis(OH) anthraquinone | 63285 | 1 |
| Disperse Blue 60 | 1,4-bis(NH₂)-2-C(O)-3-CH₂-N(CH₂)₃OCH₃ anthraquinone | 61104 | 1 |
| Disperse Blue 62 | Anthraquinone | | 1 |
| Disperse Blue 64 | Anthraquinone | | 1 |
| Disperse Blue 72 | 1-OH-4-NH(4-tolyl) anthraquinone | 60725 | 1 |
| Disperse Blue 77 | Anthraquinone | 60766 | 1 |

TABLE II-continued

| Dye | Formula/Chemical Class | C.I. # | Toning Ability |
|---|---|---|---|
| Disperse Blue 79 | Azo | 11345 | 1 |
| Disperse Blue 87 | Anthraquinone | | 1 |
| Disperse Blue 94 | (structure shown) | | 1 |
| Disperse Blue 109 | Anthraquinone | | 1 |
| Disperse Blue 153 | Anthraquinone | | 1 |
| Disperse Blue 180 | Anthraquinone | | 1 |
| Disperse Blue 183 | Azo | | 1 |
| Disperse Blue 287 | Azo | | 1 |
| Disperse Blue 326 | Anthraquinone | | 1 |
| Disperse Blue 333 | | | 1 |
| Disperse Blue 337 | (structure shown) | 11337 | 1 |
| Disperse Blue 360 | Azo | | 1 |
| Disperse Blue 367 | Azo | | 1 |
| Disperse Green 9 | | | 1 |
| Disperse Violet 8 | Anthraquinone | 62030 | 1 |
| Disperse Violet 17 | (structure shown) | 60712 | 1 |
| Disperse Violet 26 | (structure shown) | 62025 | 1 |
| Disperse Violet 28 | (structure shown) | 61102 | 1 |
| Disperse Violet 33 | Anthraquinone | 11218 | 1 |
| Disperse Violet 35 | Anthraquinone | | 1 |
| Disperse Violet 36 | Anthraquinone | | 1 |
| Disperse Violet 40 | Azo | | 1 |

TABLE II-continued

| Dye | Formula/Chemical Class | C.I. # | Toning Ability |
|---|---|---|---|
| Disperse Violet 48 | | | 1 |
| Disperse Violet 60 | Azo | | 1 |
| Disperse Violet 63 | Azo | | 1 |
| Disperse Violet 72 | | 60725 | 1 |
| Disperse Violet 91 | | | 1 |

Each of the Disperse dyes listed in Tables 1 & 2 above may be available commercially under one or more of the following trade names which are listed in Table 3 below. The list, by no means, includes all suppliers of these Disperse dyes.

TABLE III

| Tradename | Supplier | Tradename | Supplier |
|---|---|---|---|
| Adis | Aashiana Dyestuffs | ADC | American Dyestuff |
| Akasperse | Aakash Chemicals & Dyestuffs | Albacel | Albanil Dyestuff |
| Albasperse | Albanil Dyestuff | Allilon | Allied Industrial |
| Amecron | American Dyestuff | Appolon | Teiheung |
| Bezjian | Bezjian Dye-Chem | Carsperse | Carey Industries |
| Caracet | Caroline Color & Chemical Co. | Carester | Carolina Color & Chemical Co. |
| Dianix | Dystar | Dispersol | Zeneca Colors |
| Dispersrite | Rite Industries | Dorospers | D & G Dyes |
| Elcosperse | Rite Industries | Foron | Sandoz Chemicals |
| Imperse | Impa Overseas | Intrasil | Crompton & Knowles |
| Intrasperse | Crompton & Knowles | Intratherm | Crompton & Knowles |
| Isosperse | Isochem | Leadisperse | Leadertech Colors |
| Morcron | Morlot Color & Chemical | Morsperse | Morlot Color & Chemical |
| Orcocil | Organic Dyestuff | Orcocilacron | Organic Dyestuff |
| Palanil | BASF | Patcosperse | C. H. Patrick & Co. |
| Polysperse | Dyerich Chemical | Resolin | Dystar |
| Serilene | Yorkshire Pat-Chem | Sodyecron | Sandoz Chemicals |
| Spectro | Spectro Color & Chemical | Suprasperse | Dyerich Chemical |
| Taicron | T & T Industries | | |

Some Disperse dyes have been used as color enhancing agents in conjunction with other hair colorants such as Direct dyes. However, they have never been used by themselves before to color the hair, and they have never been used in a category-2 bleach medium prior to this invention. U.S. Pat. No. 3,578,387 teaches of an alkaline hair coloring composition which contained water-soluble Direct dyes and Disperse dyes, in addition to a hydrogen peroxide solution which is mixed with these dyes just before use. The hydrogen peroxide serves in the alkaline medium as a mild bleach. This composition, in all aspects is a category-1 bleach. The same composition, however, fails dramatically in a stronger category-2 bleach medium. To demonstrate this point, the ashing Disperse dyes (blue and violet) specified in the patent, were tested in both, category-1 and category-2 bleaching media. The test consisted of treating natural white hair swatches with 1% mixtures of Disperse Blue 1, prepared in either an alkaline creme hair color base and mixed with 6% hydrogen peroxide, (category-1 medium), or a bleach powder (Clairol's Basic White 2, category-2 medium). The hair swatches were incubated for 10 minutes at 55° C. The same tests were repeated with Disperse Violet 4. Disperse Blue 19 could not be sourced and is now apparently out of production.

Any color which was deposited on the hair swatches in either medium, was measured on a computerized spectrophotometer (Spectraflash, SF 600, Datacolor International, Charlotte, N.C., USA). The readings are based on the CIELAB color difference equation, using a natural white hair swatch bleached in the absence of any dyes as a standard (light source D65, 10° observer). The intensity of any deposited blue hue is based on the magnitude of the negative $Db^*$ value (color space $b^*$ axis, negative values indicate blue, positive values indicate yellow), while a red hue intensity is related to a positive $Da^*$ value ($a^*$ axis, positive values indicate red, negative values indicate green). Thus a sample can be judged as bluer, more yellow, greener or redder than the standard. The scale is an absolute value ranging from 0 to 100, where 0 indicates no color intensity and 100 is maximum color intensity.

Figure 2:
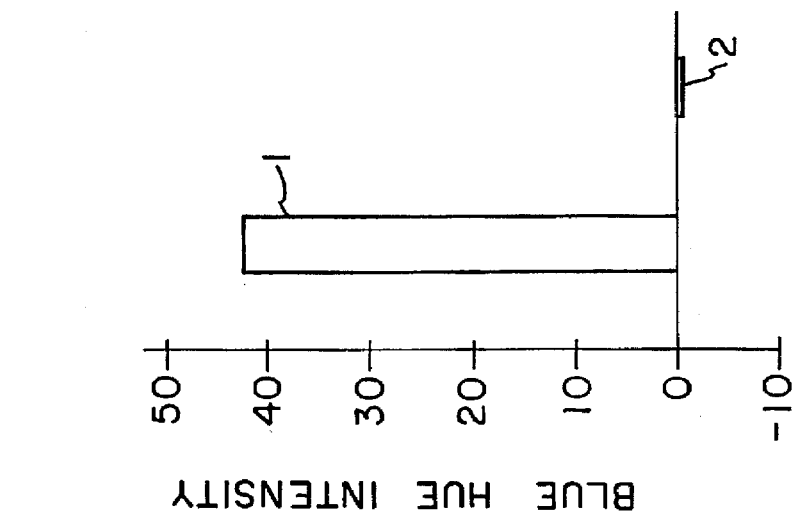
FIG. 2 is a plot of the stability of Disperse Violet 4 in the two bleach mediums of FIG. 1.
Figure 1:
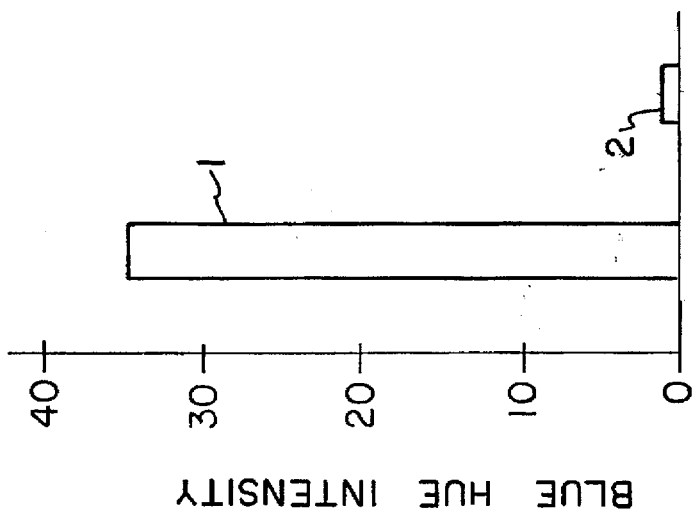
FIG. 1 is a plot of the stability of Disperse Blue 1 in a Category-1 Bleach and in a Category-2 Bleach.

The data presented in Table 4, and in FIGS. 1 & 2, demonstrate the performance of the drabbing Disperse dyes specified in U.S. Pat. No. 3,578,387 in either bleach category: Alkaline color base plus peroxide (category-1), or powder bleach base plus peroxide (category-2). It is evident that the toning capacity of these disperse dyes, as indicated by the intensity of the blue hue, is non-existent in a category-2 bleach medium. In all of the figures below, and for graphing purposes, the sign on all $Db^*$ readings has been reversed.

Figure 4:
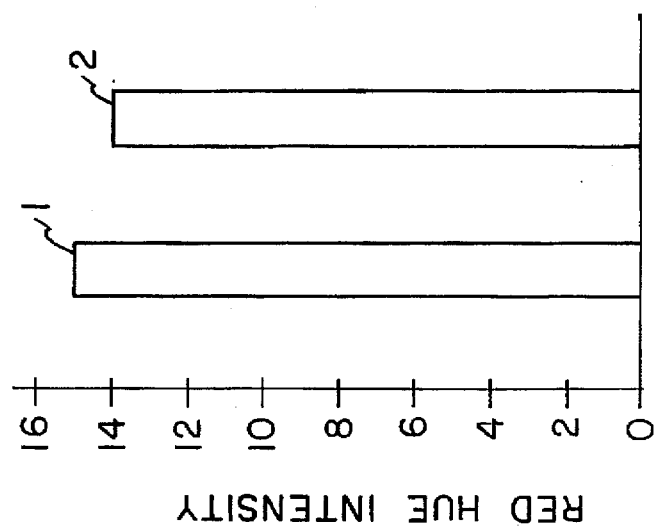
FIG. 4 is a plot of the stability of Disperse Red 338 in the two bleach mediums of FIG. 1.

In comparison to Disperse Blue 1 and Disperse Violet 4, the disperse dyes utilized by the present invention are stable and with abundant toning capacity in either medium. For example, FIG. 3 shows the performance of Disperse Blue 148, while FIG. 4 shows that of Disperse Red 338 which can be used in conjunction with Disperse Blue 148 to create a violet hue.

TABLE IV

| Disperse Dyes in U.S. Pat. No. 3,578,387 | Performance in Category-1 Bleach | Performance in Category-2 Bleach |
|---|---|---|
| Disperse Blue 1 | Stable, deep blue color on natural white hair | Unstable, dye is destroyed in minutes, no color deposited on natural white hair |
| Disperse Violet 4 | Stable, violet color on natural white hair | Unstable, dye is destroyed in minutes, no color deposited on natural white hair |

Figure 5:
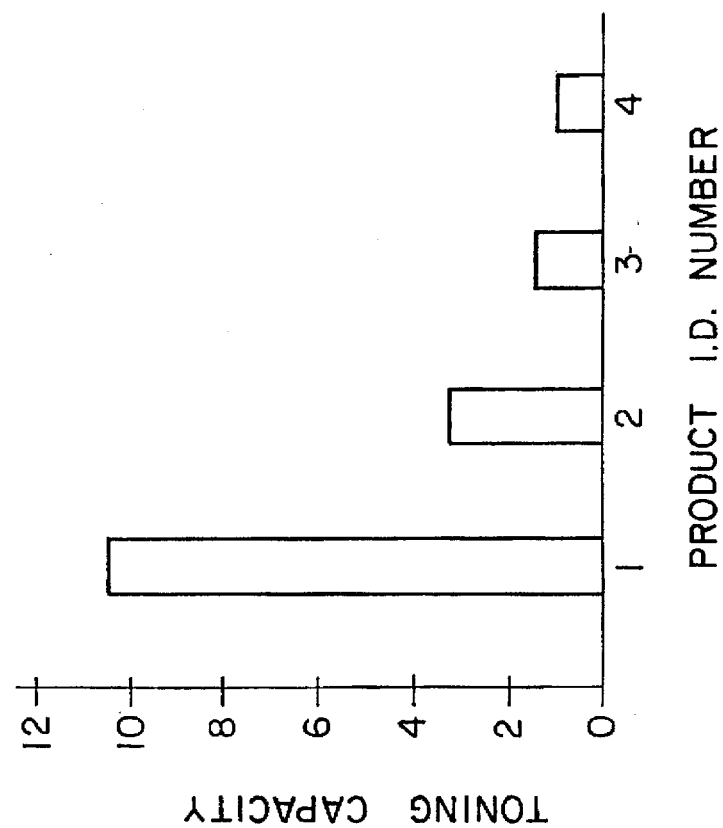
FIG. 5 is a plot of the toning capacity of some pigmented commercial Category-2 hair bleaches in comparison to the present invention, wherein (1) is Example 4 of the present invention; (2) is commercially purchased Kaleidocolors Blue (Kaleidocolors is a Trademark of Clairol, Inc. of Stamford, Conn.); (3) is commercially purchased Ultraglitz Blue Violet (Ultraglitz is a Trademark of Farouk Systems, Inc., Houston, Tex.) (U.S. Pat. No. 5,224,964); and (4) is U.S. Pat. No. 2,991,228 (Example #1).

The toning capacity of one of the formulations of the present invention (Example 4 below) was compared to that of some professional commercial compositions, under identical conditions. Natural white hair was bleached with the different formulations, and the blue hue was measured as mentioned above. FIG. 5 shows the enhanced toning achieved with this invention. To make the data meaningful, it should be pointed out that a test sample should be at least 8 $Db^*$ units bluer than the standard, in order for the brassy undertones in bleached medium brown hair to be drabbed or toned to a pleasing natural color. The data in FIG. 5 indicate that the present invention, unlike the commercial formulations cited, has sufficient toning capacity to eliminate any warmth that the bleaching process may generate.

In what follows, specific examples will be cited to illustrate the applicability of the present invention. It will be obvious, of course, that because of the large number of potential dye combinations, only a few examples can be cited. Example 1 shows a bleach powder base which was used to incorporate the dyes to form compositions which could simultaneously lighten the color of the hair and neutralize any warm undertones. Numerous variations are possible on the bleach base, including amounts of active ingredients and types of surfactants, thickeners, fillers, or other additives. Similarly, the powder base could be made into a creme form by adding any of a multitude of hydrophobic solvents (e.g. mineral oil), and emulsifiers.

Example 2 presents a dye combination which can be used to neutralize undertones resulting when light brown or dark blond hair are lightened. Example 3 demonstrates toning effects on medium brown hair. Example 4 shows same effects on dark brown hair, while Example 5 provides an illustration of how a medium brown hair can be transformed into an auburn hair in a single step. Traditionally, a two-step process has always been required to change the color of hair from brown to auburn.

EXAMPLE 1

Bleach Powder Base

Potassium persulfate 28.0
Ammonium persulfate 20.0
Sodium silicate 24.0
Magnesium oxide 14.5
Hydroxyethyl cellulose 5.0
Soap beads 6.0
Silica 2.0
Disodium EDTA 0.5

EXAMPLE 2

Lightening and Toning of Light Brown Hair

Bleach Base of Example 1 99.3%
Disperse Blue 281 0.5
Disperse Violet 26 0.2

The above powder mixture was mixed in the ratio of 1:4 with 6% hydrogen peroxide solution (1 part powder-dye mixture: 4 parts peroxide) to yield a smooth creme, applied to light brown hair, and placed for 10 minutes at 55° C. Result: Hair was lightened to pale silver blond.

EXAMPLE 3

Lightening and Toning of Medium Brown Hair

Bleach Base of Example 1 99.7%
Disperse Blue 102 0.1
Disperse Blue 148 0.1
Disperse Red 338 0.1

The bleach mixture above was mixed with peroxide and applied to medium brown hair. Conditions were the same as in Example 2. Result: Hair acquired a light natural blond tone with no undesirable warmth.

EXAMPLE 4

Lightening and Toning of Dark Brown Hair

Bleach Base of Example 1 99.65%
Disperse Blue 148 0.15
Disperse Blue 106 0.10
Resolin Blue K 0.10

The above bleach mixture was used on dark brown hair. Conditions were the same as in Example 2. A natural blond color was obtained. No reddish or warm undertones were noticed.

EXAMPLE 5

One-Step Transformation of Brown Hair to Auburn

Bleach Base of Example 1 97.5%
Disperse Orange 3 0.5
Disperse Red 338 2.0

The above mixture was used on medium brown hair. Same conditions as in Example 2. Hair color was transformed into a pleasant golden auburn tone.

Discussion

Therefore, what has been shown is that two classes of dyes have been shown to be both oxidatively stable and effective in coloring hair. The first family is the anthraquinones, which are typically synthesized by ring closure procedures involving adaptations of Friedel-Crafts acylations, typically involving phthalic anhydride or its derivatives and benzene. Substituted derivatives are usually synthesized by the utilization of a substituted benzene as the reactant. Initial acylations typically result in para substitution, and if this position is blocked, ortho acylation is possible. Polynuclear compounds are also possible through the use of naphthalene or its derivatives. The second family is that of the azo compounds, often synthesized from diazonium salts reacting with various aromatic compounds. In this reaction, known as coupling, the nitrogen of the diazonium group is retained in the product. The aromatic ring undergoing attack by the diazonium ion must, in general, contain a powerfully electron-releasing group, generally —OH, —NR$_2$, —NHR, or —NH$_2$. Substitution usually occurs para to the activating group. The coupling is electrophilic aromatic substitution in which the diazonium ion is the attacking agent. The azo compounds are strongly colored, and can be intensely yellow, orange, red, blue or even green, depending upon the exact structure of the molecule.

In general, the anthraquinones will have the following generic base formula, as shown by formula (I).

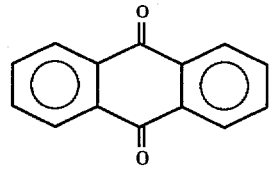

Specific dyes within this family will have substituents at various positions, as are shown in generic formula (II)

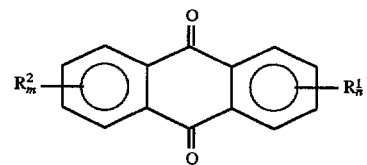

and wherein R$^1$ and R$^2$ are independently selected from the group consisting of:

$NR^3{}_2$ wherein
  each $R^3$ are independently selected from the group consisting of:
    $C_{1-4}$ alkyl,
    $C_{1-4}$ substituted alkyl,
      wherein the substituents are selected from the group consisting of $OR^4$ and X, wherein
        $R^4$ is selected from the group consisting of:
          H and $C_{1-4}$ alkyls, and
        X is a halogen;
  H,
  O,
  $C_{5-8}$ aryl,
  $C_{5-8}$ heteroaryl wherein the heteroatom is N,
  $C_{5-8}$ substituted aryl and $C_{5-8}$ substituted heteroaryl
    wherein the substituents are selected from the group consisting of:
      $C_{1-4}$ alkyl,
      $C_{1-4}$ substituted alkyl,
        wherein the substituents are selected from the group consisting of $OR^4$ and X as defined previously, and
      carboxyl;
  $OR^3$ wherein $R^3$ is as defined previously;
  X;
m is an integer from 0 to 3 inclusive; and
n is an integer from 1 to 4 inclusive.

In general, the azo dyes will have the following generic base formula, as shown by formula (III).

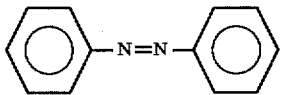

Specific dyes within this family will have substituents at various positions, as are shown in generic formula (IV)

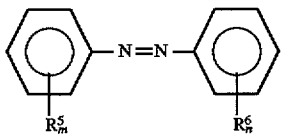

and wherein $R^5$ and $R^6$ are independently selected from the group consisting of:

$N(R^7)_2$ wherein
  each $R^7$ are independently selected from the group consisting of:
    $C_{1-4}$ alkyl,
    $C_{1-8}$ substituted alkyl,
      wherein the substituents are selected from the group consisting CN, $(OR^8)_y$, $O(O)CR^8$ and X, wherein
        $R^8$ is selected from the group consisting of:
          H and $C_{1-4}$ alkyls,
        X is a halogen, and
        y is an integer from 1 to 3 inclusive;
  H, and
  O;
CN;
X;
m is an integer from 1 to 3 inclusive; and
n is an integer from 1 to 4 inclusive.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A composition for simultaneously lightening and coloring hair which comprises:
   a Category-2 bleach which comprises a persulfate salt, wherein said bleach is present in an amount sufficient to lighten the color of the hair, and wherein said bleach is sufficient to lighten the color of the hair by up to seven levels; and
   an oxidatively stable Disperse dye selected from the group consisting of azo and anthraquinone dyes.

2. The composition of claim 1 wherein the anthraquinone dye has a structural unit as shown in formula (I)

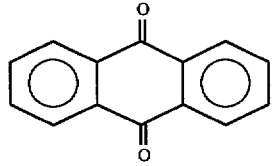

and the azo dye has a structural unit as shown in formula (III).

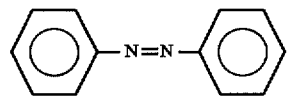

3. The composition of claim 2 wherein the anthraquinone dye has a structural unit as shown in formula (II)

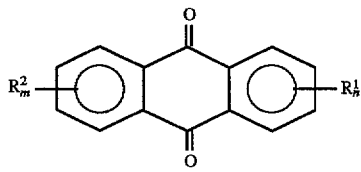

and wherein $R^1$ and $R^2$ are independently selected from the group consisting of:

$NR^3{}_2$ wherein
  each $R^3$ are independently selected from the group consisting of:
    $C_{1-4}$ alkyl,
    $C_{1-4}$ substituted alkyl,
      wherein the substituents are selected from the group consisting of $OR^4$ and X, wherein
        $R^4$ is selected from the group consisting of:
          H and $C_{1-4}$ alkyls, and
        X is a halogen;
  H,
  O,
  $C_{5-8}$ aryl,
  $C_{5-8}$ heteroaryl wherein the heteroatom is N,
  $C_{5-8}$ substituted aryl and $C_{5-8}$ substituted heteroaryl
    wherein the substituents are selected from the group consisting of:
      $C_{1-4}$ alkyl,
      $C_{1-4}$ substituted alkyl,
        wherein the substituents are selected from the group consisting of $OR^4$ and X as defined previously, and carboxyl;

OR$^3$ wherein R$^3$ is as defined previously;

X is a halogen;

m is an integer from 0 to 3 inclusive; and n is an integer from 1 to 4 inclusive, and
the azo dye is as shown in generic formula (IV)

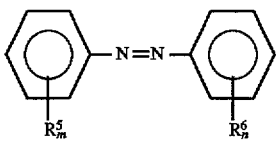

and wherein R$^5$ and R$^6$ are independently selected from the group consisting of:

N(R$^7$)$_2$ wherein each R$^7$ are independently selected from the group consisting of:
- C$_{1-4}$ alkyl,
- C$_{1-8}$ substituted alkyl,
  wherein the substituents are selected from the group consisting CN, (OR$^8$)$_y$, O(O)CR$^8$ and X, wherein
  R$^8$ is selected from the group consisting of:
  - H and C$_{1-4}$ alkyls,
  - X is a halogen, and
  - y is an integer from 1 to 3 inclusive;
- H, and
- O;

CN;

X is a halogen;

m is an integer from 1 to 3 inclusive; and n is an integer from 1 to 4 inclusive.

4. The composition of claim 3 wherein the dye is selected from the group consisting of Disperse Blue dyes, Disperse Red dyes, Disperse Orange dyes, Disperse Violet dyes, Disperse Green dyes, Disperse Yellow dyes, and mixtures thereof.

5. A method for simultaneously lightening and coloring hair which comprises:

mixing a Category-2 bleach which comprises a persulfate salt with an oxidatively stable Disperse dye selected from the group consisting of azo and anthraquinone dyes and applying to the hair, wherein said bleach is present in an amount sufficient to lighten the color of the hair, and wherein said bleach is sufficient to lighten the color of the hair by up to seven levels.

6. The method of claim 5 wherein the anthraquinone dye has a structural unit as shown in formula (I)

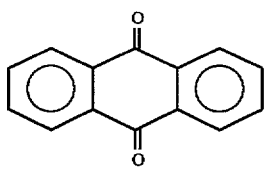

and the azo dye has a structural unit as shown in formula (III).

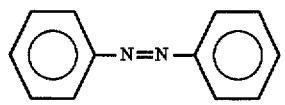

7. The method of claim 6 wherein the anthraquinone dye has a structural unit as shown in formula (II)

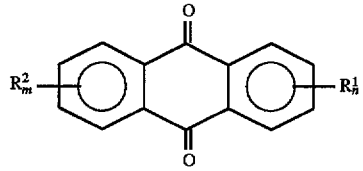

and wherein R$^1$ and R$^2$ are independently selected from the group consisting of:

NR$^3$$_2$ wherein each R$^3$ are independently selected from the group consisting of:
- C$_{1-4}$ alkyl,
- C$_{1-4}$ substituted alkyl,
  wherein the substituents are selected from the group consisting of OR$^4$ and X, wherein
  R$^4$ is selected from the group consisting of:
  - H and C$_{1-4}$ alkyls, and
  - X is a halogen;
- H,
- O,
- C$_{5-8}$ aryl,
- C$_{5-8}$ heteroaryl wherein the heteroatom is N,
- C$_{5-8}$ substituted aryl and C$_{5-8}$ substituted heteroaryl wherein the substituents are selected from the group consisting of:
  - C$_{1-4}$ alkyl,
  - C$_{1-4}$ substituted alkyl,
    wherein the substituents are selected from the group consisting of OR$^4$ and X as defined previously, and
- carboxyl;

OR$^3$ wherein R$^3$ is as defined previously;

X is a halogen;

m is an integer from 0 to 3 inclusive; and n is an integer from 1 to 4 inclusive, and
the azo dye is as shown in generic formula (IV)

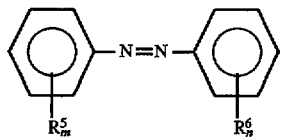

and wherein R$^5$ and R$^6$ are independently selected from the group consisting of:

N(R$^7$)$_2$ wherein each R$^7$ are independently selected from the group consisting of:
- C$_{1-4}$ alkyl,
- C$_{1-8}$ substituted alkyl,
  wherein the substituents are selected from the group consisting CN, (OR$^8$)$_y$, O(O)CR$^8$ and X, wherein
  R$^8$ is selected from the group consisting of:

H and $C_{1-4}$ alkyls,
X is a halogen, and
y is an integer from 1 to 3 inclusive;
H, and
O;
CN;
X is a halogen;
m is an integer from 1 to 3 inclusive; and
n is an integer from 1 to 4 inclusive.

8. The method of claim 7 wherein the dye is selected from the group consisting of Disperse Blue dyes, Disperse Red dyes, Disperse Orange dyes, Disperse Violet dyes, Disperse Green dyes, Disperse Yellow dyes, and mixtures thereof.

9. A method for simultaneously lightening and coloring hair which comprises:
mixing a Category-2 bleach which comprises a persulfate salt in an amount sufficient to lighten the color of the hair, wherein said bleach is sufficient to lighten the color of hair by up to seven levels;
applying the bleach to the hair; and
applying an oxidatively stable Disperse dye selected from the group consisting of azo and anthraquinone dyes to the hair.

10. The method of claim 9 wherein the anthraquinone dye has a structural unit as shown in formula (I)

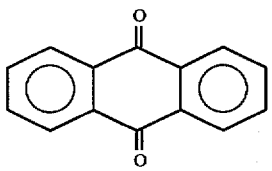

and the azo dye has a structural unit as shown in formula (III).

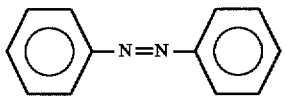

11. The method of claim 10 wherein the anthraquinone dye has a structural unit as shown in formula (II)

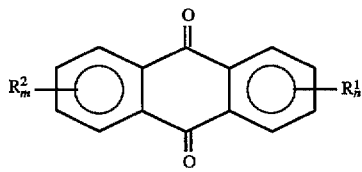

and wherein $R^1$ and $R^2$ are independently selected from the group consisting of:

$NR^3_2$ wherein
each $R^3$ are independently selected from the group consisting of:
$C_{1-4}$ alkyl,
$C_{1-4}$ substituted alkyl,
wherein the substituents are selected from the group consisting of $OR^4$ and X, wherein
$R^4$ is selected from the group consisting of:
H and $C_{1-4}$ alkyls, and
X is a halogen;
H,
O,
$C_{5-8}$ aryl,
$C_{5-8}$ heteroaryl wherein the heteroatom is N,
$C_{5-8}$ substituted aryl and $C_{5-8}$ substituted heteroaryl wherein the substituents are selected from the group consisting of:
$C_{1-4}$ alkyl,
$C_{1-4}$ substituted alkyl,
wherein the substituents are selected from the group consisting of $OR^4$ and X as defined previously, and
carboxyl;
$OR^3$ wherein $R^3$ is as defined previously;
X is a halogen;
m is an integer from 0 to 3 inclusive; and
n is an integer from 1 to 4 inclusive, and
the azo dye is as shown in generic formula (IV)

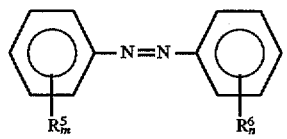

and wherein $R^5$ and $R^6$ are independently selected from the group consisting of:

$N(R^7)_2$ wherein
each $R^7$ are independently selected from the group consisting of:
$C_{1-4}$ alkyl,
$C_{1-8}$ substituted alkyl,
wherein the substituents are selected from the group consisting CN, $(OR^8)_y$, $O(O)CR^8$ and X, wherein
$R^8$ is selected from the group consisting of:
H and $C_{1-4}$ alkyls,
X is a halogen, and
y is an integer from 1 to 3 inclusive;
H, and
O;
CN;
X is a halogen;
m is an integer from 1 to 3 inclusive; and
n is an integer from 1 to 4 inclusive.

12. The method of claim 11 wherein the dye is selected from the group consisting of Disperse Blue dyes, Disperse Red dyes, Disperse Orange dyes, Disperse Violet dyes, Disperse Green dyes, Disperse Yellow dyes, and mixtures thereof.

* * * * *